United States Patent [19]

Chambers

[11] Patent Number: 4,906,461

[45] Date of Patent: Mar. 6, 1990

[54] HAIR TREATMENT COMPOSITION

[76] Inventor: Warren Chambers, 637 DeKalb Pike, King of Prussia, Pa. 19406

[21] Appl. No.: 274,293

[22] Filed: Nov. 21, 1988

[51] Int. Cl.[4] .............................................. A61K 7/075
[52] U.S. Cl. ........................................ 424/74; 424/70; 424/105; 424/195.1; 514/783
[58] Field of Search ...................... 424/74, 105, 195.1, 424/70; 514/783

[56] References Cited

U.S. PATENT DOCUMENTS 4,494,557 1/1985 Nagal ................................ 424/70 X
4,658,839 4/1987 Dallal et al. ...................... 424/70 X

FOREIGN PATENT DOCUMENTS 2510402 2/1983 France .................................. 424/74

OTHER PUBLICATIONS

Chemical Abstracts, CA:90700a, vol. 70, 1969, p. 237.

*Primary Examiner*—Ellis P. Robinson
*Assistant Examiner*—Susan S. Rucker
*Attorney, Agent, or Firm*—Benasutti

[57] ABSTRACT

A hair treatment which replaces properties of hair which has been treated with a chemical treatment such as perming, coloring or straightening is disclosed. The present invention may be formulated with a neutral base solution for use with present cream moisturizers for home use. Also, the present invention may be formulated with an acidic base for use by professionals in finishing chemical treatments such as permanents and coloring.

6 Claims, No Drawings

HAIR TREATMENT COMPOSITION

FIELD OF INVENTION

The present invention relates to a hair treatment composition which replaces hair properties affected by chemical treatment. More particularly the present invention relates to a hair treatment composition which may be used in combination with conventional conditioners as well as with chemical treatments such as coloring and perms.

BACKGROUND

The use of chemical treatment processes for hair, such as coloring, bleaching and permanent waving or curling, can adversely affect the texture and condition of hair. This can make it difficult to curl, cut and manage the hair during styling as well as during regular care. Many hair conditioner treatments to soften the hair or cream rinses are applied to the hair as a separate step to remedy this problem. Softening agents such as cationic fatty quaternary compounds have been used extensively in such conditioning rinses. Typically such conditioners were not effective when incorporated into hair treatment compositions such as shampoos, coloring, and permanent wave compositions.

Hair conditioning or softening compositions which are compatible, that is may be mixed with other hair treatment compositions such as shampoos, coloring and permanent waving compositions, have been developed. U.S. Pat. No. 4,579,131 disclosed an aqueous hair treatment compound which is compatible with curling, waving coloring, shampoos and other hair treating compositions. U.S. Pat. No. 4,579,131 adds a water soluble cationic polymer obtained by the polymerization of epihalohydrins and an alkylene polyamine. The cationic polymer can be combined with a variety alkyline or acidic hair treatment compositions to act as a hair softener.

U.S. Pat. No. 4,610,874 discloses a hair conditioner which comprises a combination of derivatives of ethoxylated/acetylated lanolins with cationic polymers and hydroxyethyl cellulose which may be blended with other hair conditioner materials to control reagent buildup on the hair.

U.S. Pat. No. 4,507,280 discloses a hair treatment composition which contains a cationic polymer having at least one positively charged nitric or sulfuric moiety in each repeating unit, an amphoteric surfactant product and a betaine. The composition is a conditioning complex which adheres to the hair and resists the effects of several subsequent shampooings.

Thus, the use of cationic surfactants in conjunction with certain fatty materials such as lanolin, mineral oils or alcohols as well as ionic polymers may be employed as hair conditioners. The use of organosilicone compounds in hair conditioners is disclosed in U.S. Pat. No. 4,601,902.

However a hair conditioner which may be employed in combination with either cream based conditioners or chemical treatment solutions and which replace the properties that are affected by other hair treatment processes have been heretofore unavailable.

SUMMARY OF THE INVENTION

The present invention is directed to a hair treatment composition which is effective at repairing hair which has been damaged by chemical treatment. The hair treatment composition of the present invention comprises a mixture of natural ingredients which may be employed in conjunction with known, wet hair conditioners and after shampoos as well as in conjunction with professional chemical hair treatments. The composition of the present invention includes an aqueous mixture which may be used in conjunction with other hair processing treatments. The composition may be rendered acidic by the addition of ammonium alum which allows the composition to be readily employed in conjunction with professional chemical treatments such as coloring, straightening and permanent waving. The composition is specifically formulated to repair or replace the damage typically caused by such chemical treatments.

DETAILED DESCRIPTION OF THE INVENTION

The composition of the present invention is formulated by dissolving epsom salt in purified water preferably de-ionized water. Thereafter, sodium bicarbonate and powdered sea kelp are added. To this mixture, cider vinegar is added and finally placenta extract or a placenta extract composition such as Hask placenta is added.

For every five gallon batch of the final composition, preferably from about 4 to about 8 dry volume cups of epsom salt are used. Most preferably, the composition comprises 6 dry volume cups of epsom salt per five gallon batch. The addition of the epsom salt serves to boost the pH of the final composition to the desired neutral pH range.

Preferably, from about 3.5 to about 10.5 dry volume ounces of sodium bicarbonate are used in the preparation of a five gallon batch of the final composition. Most preferably, seven dry volume ounces of sodium bicarbonate are used.

Preferably, at least about three dry volume ounces of sea kelp are added to formulate a five gallon batch of the final composition. Most preferably, 3.5 dry volume ounces of powdered sea kelp are used. The sea kelp is preferably Icelandic sea kelp which has been processed into a powdered form. This may be achieved by flash freezing and pulverizing the sea kelp to obtain a dry powder. Icelandic sea kelp powder is generally available. It is believed that the addition of the sea kelp imparts beneficial properties to the composition which promote the tensile strength and elasticity of the hair when the composition is used thereon.

A five gallon batch of the present composition will preferably comprise from about 32 to about 48 fluid ounces of cider vinegar, preferably apple cider vinegar. Most preferably, a five gallon batch comprises about 40 fluid ounces of cider vinegar. Typically, cider vinegar comprises between four to six per cent acetic acid. In the present invention, apple cider vinegar comprising five percent acetic acid is preferred.

The compositions of the present invention comprises a placenta extract component. The placenta extract comprises liquid and semi-solid material centrifugally removed from supranatant placenta such as human or bovine placenta. The placenta extract may be added to the present composition as a commercially available placenta extract composition such as the Hask Placenta product (hereinafter referred to a "Hask placenta") available from Hask, Inc. of Great Neck, New York. A five gallon batch of the present composition preferably contains between about 4.375 to about 5.625 fluid ounces of Hask placenta, most preferably 5 fluid ounces. Pure placenta extract may be used in the present compositions in lieu of Hask placenta in amounts equivalent to the placenta component found in the Hask placenta product.

The pH of the present compositions is preferably adjusted within the pH range of from about 6.0 to about 7.5. Most preferably, the pH is adjusted to abut 7.2 Adjustment of the pH is accomplished by varying the amounts of epsom salt, sodium bicarbonate and vinegar components within the ranges set forth above. Compositions with neutral pH's may be distributed to consumers for use at home.

The present invention also contemplates compositions having a pH of about 4.5 for use by professional hairstylers in conjunction with acidic hair treatments such as perming. The acidic composition of the present invention may be obtained by the addition of sufficient ammonium alum to the above identified neutral compositions to adjust the composition to the desired acid pH. For example, this may be accomplished by adding 1.5 dry volume teaspoons of ammonium alum per eight fluid ounces of the neutral pH compositions.

In use, the compositions of the present invention provide many beneficial advantages. When applied to the hair in combination with other treatments, the compositions decrease damage to the hair from the treatments. When applied separately, the compositions repair hair damage caused by other treatments such as perming and coloring. Application of the compositions prevents chemical burn of the hair, improves the tensile strength and elasticity of the hair, promotes the sheen and softness the hair, reduces scalp burning and irritation, increases manageability and body of the hair, decreases frizzing of the hair and rejuvenates the hair. The hair treatment compositions are generally compatible with major brands of perms and colors. When used by professional hairdressers, the compositions also reduce irritation to the hands of the hairdresser associated with the application of other treatments.

The hair treatment compositions of the present invention may be applied to hair either alone or in combination with other chemical treatments. When no other chemical treatments are applied to the hair, it is preferred to spray mist the composition onto the hair until the hair becomes saturated. The treatment is permitted to remain on the hair for a period of time either at ambient temperature (for about 10 or more minutes) or with the addition of heat (for about 2 to 5 minutes). Thereafter, the hair is rinsed thoroughly.

When the treatment compositions of the present invention are applied to hair in combination with other chemical treatments such as permanent waving, coloring and conditioning treatments, they may be applied before and/or after the application of the other treatments for a period of time as set forth above. The treatment compositions may also be added directly to other chemical treatment compositions such as perm, peroxide, bleach and coloring solutions.

To further aid in the understanding of the present invention, and not by way of limitations, the following examples are presented.

EXAMPLE 1

A hair treatment composition is prepared by combining:

| | |
|---|---|
| Epsom Salt | 6 dry vol. cups |
| Sodium Bicarbonate | 7 dry vol. ounces |
| Apple cider vinegar | |
| (5% acetic acid) | 40 fluid ounces |
| Powdered Icelandic sea kelp | 3.5 dry vol. ounces |
| Hask placenta | 5 fluid ounces |
| De-ionized water | Remainder |
| Total | 5 gallons |

A hair treatment composition having a pH of 7.2 is obtained.

EXAMPLE 2

A hair treatment composition is prepared by adding 1.5 volume teaspoons of ammonium alum to 8 fluid ounces of the composition of Example 1. A hair treatment composition having a pH of 4.5 is obtained.

EXAMPLE 3

In the treatment of damaged or processed hair to obtain permanent waving, a conventional perm solution is reduced by one fluid ounce. One fluid ounce of the hair treatment composition of Example 2 is added to the perm solution and mixed therewith. The thusly modified perm composition is applied to hair which is set on perm rods in accordance with the normal application of perm solution. The hair is then rinsed and blotted dry with a towel. Thereafter, the hair is saturated by spraying a mist of the composition of Example 1 on the hair and then blotted with a towel. A conventional neutralizer solution for the perm treatment is then applied. The hair is thoroughly rinsed and the perm rods removed.

EXAMPLE 4

In the treatment of damaged or processed hair to obtain permanent waving, a composition prepared in accordance with Example 1 is mist sprayed on hair set on perm rods until saturated. A conventional perm solution is then applied, rinsed and blotted dry with a towel as normal. Thereafter, the hair is again saturated with the composition of Example 1 and diffuse heat is applied for 3 minutes. The hair is then blotted dry with a towel and a conventional neutralizer solution for the perm treatment is applied as normal. The hair is thoroughly rinsed and the perm rods removed.

EXAMPLE 5

In the treatment of normal hair to obtain permanent waving, a conventional perm solution is applied to the hair set on perm rods. The hair is rinsed and blotted dry with a towel. The hair is then saturated by spraying a mist of the composition prepared in accordance with Example 1 onto it and allowed to stand for 15 minutes. The hair is then blotted again with a towel. Thereafter, a conventional neutralizer solution for the perm treatment is applied. The hair is thoroughly rinsed and the perm rods removed.

What is claimed is:
1. A hair treatment composition comprising:
   (a) from about 32 to about 48 fluid ounces of cider vinegar per 5 gallons of total composition;
   (b) at least about 3 dry volume ounces of powdered sea kelp per 5 gallons of total composition;
   (c) from about 4.375 to about 5.625 fluid ounces of Hask placenta per 5 gallons of total composition;
   (d) from about 4 to about 8 dry volume cups of epsom salt per 5 gallons of total compositions;

(e) from about 3.5 to about 10.5 dry volume ounces of sodium bicarbonate per 5 gallons of total composition;
(f) the remainder being purified water;
said composition having a pH in the range of from about 6.0 to about 7.5.

2. A hair treatment composition comprising:
(a) about 40 fluid ounces of cider vinegar per 5 gallons of total composition;
(b) about 3.5 dry volume ounces of powdered sea kelp per 5 gallons of total composition;
(c) about 5 fluid ounces of Hask placenta per 5 gallons to total composition;
(d) about 6 dry volume cups of epsom salt per 5 gallons of total compositions:
(e) about 7 dry volume ounces of sodium bicarbonate per 5 gallons of total composition;
(f) the remainder being purified water; said composition having a pH in the range of from about 6.0 to about 7.5.

3. A composition according to claim 1 wherein said composition has a pH of about 7.2.

4. A composition according to claim 2 wherein said composition has a pH of about 7.2.

5. A composition according to claim 1, said composition further comprising a sufficient amount of ammonium alum to adjust the pH of said composition to about 4.5.

6. A composition according to claim 2, further comprising a sufficient amount of ammonium alum to adjust the pH of said composition to about 4.5.

* * * * *